(12) United States Patent
Rafecas Jane et al.

(10) Patent No.: US 8,791,294 B2
(45) Date of Patent: Jul. 29, 2014

(54) METHOD FOR THE STEREOSELECTIVE PREPARATION OF AMINO ACID DERIVATIVES

(75) Inventors: Llorenç Rafecas Jane, Tarragona (ES); Antoni Riera Escale, Barcelona (ES); Rosario Ramon Albalate, Barcelona (ES); Monica Alonso Xalma, Barcelona (ES)

(73) Assignee: BCN Peptides, S.A., Barcelona (ES)

( * ) Notice: Subject to any disclaimer, the term of this patent is extended or adjusted under 35 U.S.C. 154(b) by 674 days.

(21) Appl. No.: 12/743,470

(22) PCT Filed: Nov. 19, 2008

(86) PCT No.: PCT/ES2008/000724
§ 371 (c)(1),
(2), (4) Date: Jul. 14, 2010

(87) PCT Pub. No.: WO2009/065987
PCT Pub. Date: May 28, 2009

(65) Prior Publication Data
US 2010/0298538 A1    Nov. 25, 2010

(30) Foreign Application Priority Data

Nov. 19, 2007   (ES) .................................. 200703112

(51) Int. Cl.
*C07C 229/36*     (2006.01)
*C07K 5/087*      (2006.01)

(52) U.S. Cl.
USPC .......................................... 562/443; 530/334

(58) Field of Classification Search
CPC ................................ C07C 227/06; C07K 1/06
See application file for complete search history.

(56) References Cited

U.S. PATENT DOCUMENTS 5,801,247 A * 9/1998 Dalton et al. .................. 548/201

OTHER PUBLICATIONS

Medina et al, Helvetica Chimica Acta, Enantioselective Syntheses of Conformationally Rigid, Highly Lipophilic Mesityl-Substituted Amino Acids, 2000, 83, pp. 972-988.*
Greene, Protective Groups in Organic Chemistry, 1981, John Wiley & Sons, Inc., New York, pp. 225-226.*
Lee et al, Bulletin of the Korean Chemical Society, Asymmetric Synthesis of Aziridines and Arylalanine Derivatives, 2005, 26(2) pp. 223-224.*
Fuson et al, Journal of the American Chemical Society, Conjugate Addition of Mesitylmagnesium Bromide to Ethyl 2,4,6-Trimethylcinnamate and to Mesitalacetomesitylene, 1950, pp. 1637-1638.*
Greene, Protective Groups in Organic Chemistry, 1981, John Wiley & Sons, Inc., New York, pp. 158-159.*
White et al, Basic Energy Sciences Advisory Committee Subpanel Workshop Report, Opportunities for Catalysis in the 21st Century, 2002, pp. 1-47.*
Medina, et al., "Enantioselective synthesis of conformationally rigid, highly lipophilic mesityl-substituted amino acids", *Helvetica Chimica ACTA*, vol. 83, 2000, pp. 972-988.
Ramon, et al., "A unified approach to mesityl amino acids based on Sharpless dihydroxylation", *Tetrahedron: Asymmetry*, 2007, vol. 18, pp. 2797-2802.
Satoh, et al., "Generation of ariridnyllithiums from sulfinylaziridines with tert-butyllithium: Properties, reactivity and application to a synthesis of alpha, alpha-dialkylamino acid esters and amides including an optically active form", *Tetrahedron*, vol. 56, 2000, pp. 4415-4425.
Xiong, et al., "Regioselective and stereoselective nucleophilic ring opening reactions of a phenyl-substituted aziridine: Enantioselective synthesis of beta-substituted Tryptophan, Cysteine and Serine derivatives", *Journal of Organic Chemistry*, vol. 67, 2002, pp. 1399-1402.

* cited by examiner

*Primary Examiner* — Paul A Zucker
(74) *Attorney, Agent, or Firm* — Foley & Lardner LLP

(57) ABSTRACT

The invention relates to a process for the stereoselective preparation of amino acid derivatives, comprising a hydrogenation reaction of the compound of formula (III), alternatively its enantiomer, wherein R is $(C_1\text{-}C_8)$-alkyl; followed by a hydrolysis reaction to obtain L-mesityl alanine, alternatively its enantiomer D-mesityl alanine and, optionally, subjecting said compound to an amino group protection reaction, particularly as Fmoc. It also comprises Fmoc-L- or Fmoc-D-mesityl alanine as products per se, useful as intermediates in preparing peptides or peptide analogs with therapeutic or biological activity.

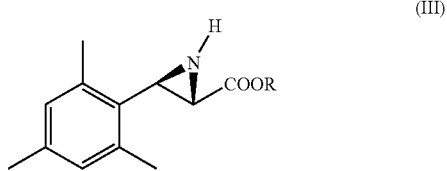

(III)

9 Claims, No Drawings

METHOD FOR THE STEREOSELECTIVE PREPARATION OF AMINO ACID DERIVATIVES

CROSS-REFERENCE TO RELATED PATENT APPLICATIONS

This application is the U.S. National Phase of PCT/ES2008/000724, filed Nov. 19, 2008, which published on May 28, 2009, as WO 2009/065987 A2, and which claims priority from Spanish Application P200703112, filed Nov. 19, 2007, all of which are incorporated herein by reference in entirety.

FIELD OF THE INVENTION

The present invention relates to a process for the stereoselective preparation of L- and D-mesityl alanine, useful for preparing peptides. More particularly, the invention relates to a process for preparing L- or D-mesityl alanine protected with an Fmoc group, as well as to said compounds per se.

BACKGROUND OF THE INVENTION

Peptide drugs represent a market of approximately 1000 million US dollars and about 1% of the total sales of active pharmaceutical ingredients. There are currently more than forty synthetic peptides in the market and more than 500 new peptide molecules are being developed.

The chemistry of peptides is a very important area of research since these compounds have interesting biological and therapeutic properties. Likewise, non-proteinogenic amino acids are increasingly more important as intermediates of said peptides with biological and therapeutic activity.

It is known that the activity of a drug depends on the conformation it is able to adopt in its interaction with the receptor and in turn, in the case of peptide compounds such conformation depends on the amino acids present in the chain. Therefore, one way of modifying their activity as drugs is to introduce conformationally restricted analogs of the amino acids forming part of the sequence of the biologically active peptide (cf. e.g. T. Osaka et al., *Current Opinion in Chemical Biology* 2002, vol. 6, pp. 809-815; D. R. Hodgson et al., *Chem. Soc. Rev* 2004, vol. 33, pp. 422-430).

The use of non-natural amino acids increases the half life of the corresponding peptides that are more easily broken down by proteases. It has also been described that the substitution of phenyl with mesityl (2,4,6-trimethylphenyl) in several amino acids considerably increases rotational barriers without significantly changing the geometry of the most stable conformer (cf. E Medina et al., *Helv. Chim. Acta* 2000, vol. 83, pp. 972-988). With this substitution of phenylalanine with mesityl alanine, peptide analogs with great biological activity have been prepared, such as analogs of [D-har8]vasopressin (cf. M. Zertova et al., *Collect. Czech. Chem. Comun.* 1993, vol. 58, pp. 2751), analgesics and antihypertensive agents (cf. EP 0213481 A2), analogs of encephalin (cf. EP 0136720 A2), analogs of the LHRH hormone (cf. EP 0049628 A1) and peptides with fibroin sequences. The preparation of those analogs has been carried out by incorporation of the amino acid protected with the Boc protecting group in racemic form and the resulting peptides have subsequently been separated by HPLC with a chiral stationary phase (cf. J. Hlavaceck et al., *Collect. Czech. Chem. Comun.*, 1991, vol. 56, p. 2991).

L-phenylalanine is a natural amino acid natural present in most natural peptides and proteins. Mesityl alanine is a non-natural amino acid useful for preparing several peptides and peptide analogs. Mesityl alanine has been prepared in racemic form and has been analytically but not preparatively separated. However, the use of mesityl alanine is rather uncommon so far, probably due to the difficulties found in preparing enantiomerically pure amino acids containing the mesityl group in the side chain.

E. Medina et al. have described a synthesis of mesityl amino acids based on Sharpless epoxidation and Sharpless aminohydroxylation (cf. *Helv. Chim. Acta* 2000, vol. 83, pp. 972-988). However, this synthesis has significant drawbacks which hinder its use on an industrial level. Among such drawbacks stands out that a very low conversion is obtained in the Sharpless epoxidation of mesityl propenol, and the crude products from the aminohydroxylation reaction need to be chromatographed to eliminate excessive residues. A synthesis of L-mesityl alanine hydrochloride by means of enantioselective asymmetric catalytic hydrogenation of an acetamidoacrylate precursor has been also described (cf. T. Li et al., *Chem. Pharm. Bull.* 2006, vol. 54, pp. 873-877).

The teachings of all these documents from the state of the art show that the research of new processes for preparing L- or D-mesityl amino acids is still an active field, particularly of L- or D-mesityl alanine, amino acids which are useful for preparing different peptides and peptide analogs with great biological activity but which have not been widely used until now due to the complexity of the known preparation processes for preparing enantiomerically pure amino acids containing this group.

DESCRIPTION OF THE INVENTION

The inventors have found a practical process with a high yield for stereoselectively preparing both L-mesityl alanine and D-mesityl alanine. The process is particularly suitable for preparing protected L- or D-mesityl alanine, which is very suitable for the solid phase synthesis of peptides.

Therefore, a first aspect of the present invention is to provide a process for the stereoselective preparation of a substantially pure enantiomer of a compound of formula (I), alternatively its enantiomer (I'),

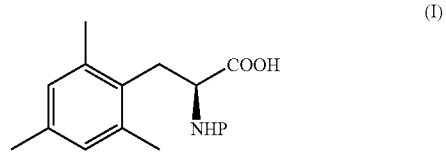

(I)

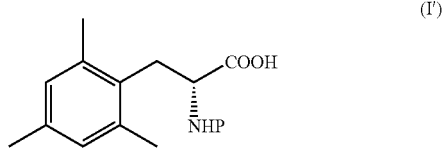

(I')

wherein P is hydrogen or an amine protecting group, comprising the following steps:

a) subjecting a compound of formula (III), alternatively its enantiomer (III'), to a hydrogenation reaction to obtain the compound of formula (II), alternatively its enantiomer (II'); wherein R is $(C_1-C_8)$-alkyl;

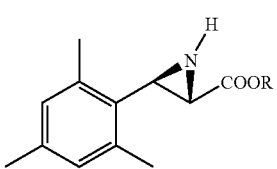
(III)

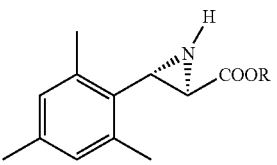
(III')

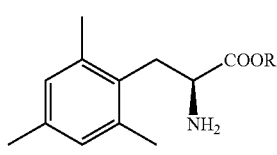
(II)

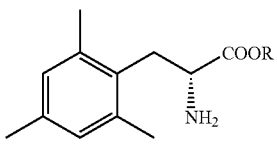
(II')

b) subjecting the compound of formula (II), alternatively its enantiomer (II'), to a hydrolysis reaction to obtain a compound of formula (I), alternatively its enantiomer (I'), wherein P is hydrogen and, optionally, subjecting said compound (I), alternatively its enantiomer (I'), to an amino group protection reaction.

Substantially pure enantiomer is understood as having an enantiomeric excess of said enantiomer equal to or greater than 95%, preferably equal to or greater than 98%, more preferably equal to or greater than 99%.

Preferably, R is a $(C_1-C_4)$-alkyl. In a particular embodiment R is methyl. In another particular embodiment, R is ethyl.

The hydrogenation step takes place with quantitative yield and complete regioselectivity. Hydrogenation is carried out by conventional methods and with the catalysts known in the state of the art, such as for example and in a non-limiting sense, metals or metal complexes. Preferably, the catalyst of the hydrogenation reaction is selected from the group consisting of the Wilkinson's catalyst, Crabtree's catalyst, Raney nickel, metals in zero oxidation state in combination with protic acids or metals from the platinum group in combination with activated carbon. More preferably, the catalyst of the hydrogenation reaction is a metal from the platinum group in combination with activated carbon, and particularly palladium/activated carbon (Pd/C). Among the sources of hydrogen for the hydrogenation reaction are included, in addition to hydrogen ($H_2$), all hydrogen donor molecules known by the person skilled in the art, such as, for example and in a non-limiting sense, hydrazine, substituted hydrazines, isopropanol or formic acid.

Hydrolysis can be carried out under basic or acidic conditions. In a preferred embodiment, hydrolysis is carried out in basic medium. Among the compounds providing a basic medium to the hydrolysis reaction is included any base known in the state of the art. In a more preferred embodiment, the base is an alkali metal hydroxide. In a particular embodiment the alkali metal hydroxide is lithium hydroxide.

The process of the present invention makes possible to protect L-mesityl alanine and D-mesityl alanine with different protecting groups. There are numerous suitable amino function protecting groups, such as carbamates, amides, sulfonamides, allyl, optionally substituted benzyl, the substituent being selected from the group consisting of $(C_1-C_8)$-alkyl, $(C_1-C_8)$-alkoxyl or halogen. The most suitable protecting groups are selected, and in a non-limiting sense, from the group consisting of t-butoxycarbonyl (BOC), 9-fluorenylmethoxycarbonyl (Fmoc), benzyloxycarbonyl (Cbz), allyl, 4-methoxybenzyl, 2,4-dimethoxybenzyl and benzyl.

In a preferred embodiment, the protecting group is the Fmoc. None of the documents in the state of the art describes L-mesityl alanine or D-mesityl alanine protected with Fmoc, Cbz, allyl, 4-methoxybenzyl, 2,4-dimethoxybenzyl or benzyl. Unlike the already known processes, the preparation process of the present invention is especially advantageous because it makes possible to obtain stereoselectively said compounds. In a particular example, protection with an Fmoc group has several advantages in the subsequent preparation of peptides from said amino acid relating to the simplicity and mild reaction conditions used in deprotecting the protecting groups and the de-anchoring of the peptides from resins. The solid phase peptide chemical synthesis strategy using the protection of amino groups with Fmoc is by far the most widely used strategy for preparing peptides on both a laboratory scale and a production scale.

The protecting group can be introduced and removed by methods known in the art (cf. *Protective Groups in Organic Synthesis*, Wiley-Interscience, (1999)). The specific conditions depend on the used protecting group. In a particular embodiment, when an Fmoc group is used, the latter can be introduced by reaction with an Fmoc-Cl or Fmoc-succinimidyl in the presence of a suitable solvent and an organic or inorganic base. Deprotection takes place in mild conditions by reaction with a base. Among the suitable bases for deprotection are included any organic or inorganic base, such as for example, and in a non-limiting sense, piperidine, morpholine, dicyclohexylamine, $K_2CO_3$ or $KHCO_3$.

In a preferred embodiment, a compound of formula (IV), alternatively its enantiomer (IV'), previously reacts with a phosphine of formula $P(R_1)_3$, wherein $R_1$ is a radical which is independently selected from the group consisting of $(C_1-C_8)$-alkyl, $(C_r-C_8)$-cycloalkyl, optionally substituted phenyl, optionally substituted —$(CH_2)n$-phenyl, wherein n is an integer from 1 to 4, and the substituents of the radicals with benzene rings are independently selected from the group consisting of $(C_1-C_8)$-alkyl, $(C_1-C_8)$-alkoxyl or halogen, to obtain the compound of formula (III), alternatively its enantiomer (III'), wherein in formulas (III), (III'), (IV) and (IV') R is $(C_1-C_8)$-alkyl.

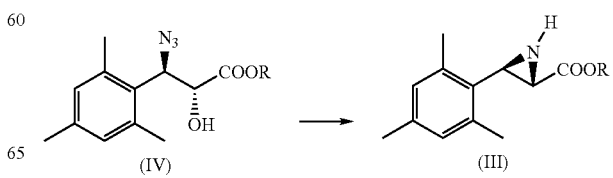

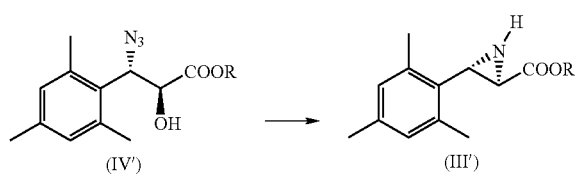

Preferably, $R_1$ are equal and the phosphine is an aromatic phosphine, and more preferably the phosphine is triphenylphosphine. This step takes place with a moderate yield but the compound is obtained in optically pure form (>99% ee by chiral HPLC).

In another preferred embodiment a compound of formula (V), alternatively its enantiomer (V'), wherein R is $(C_1$-$C_8)$-alkyl, previously reacts with an inorganic azide to obtain the compound of formula (IV), alternatively (IV'). Preferably the inorganic azide is selected from the group consisting of alkali or alkaline-earth metal azides, and particularly it is sodium azide.

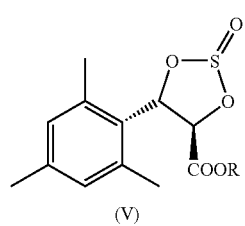

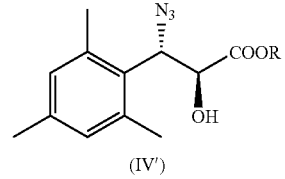

The reaction is generally carried out at a temperature comprised between 50-150° C., more preferably at a temperature of about 100° C. The opening of the sulfite ring is carried out in a completely regioselective manner and in a good yield.

In another preferred embodiment, a compound of formula (VI), alternatively its enantiomer (VI'), wherein R is $(C_1$-$C_8)$-alkyl, previously reacts with thionyl halide to obtain the compound of formula (V), alternatively its enantiomer (V'). Preferably, the thionyl halide is thionyl chloride.

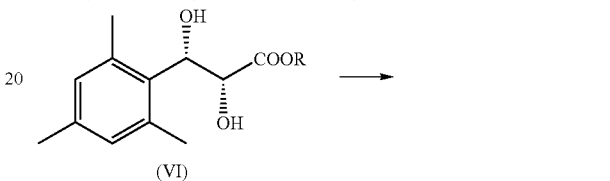

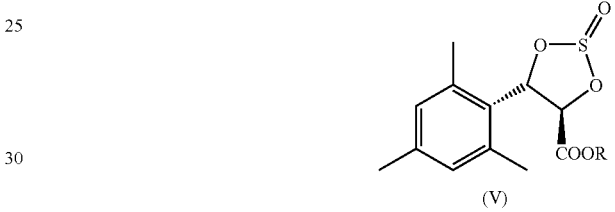

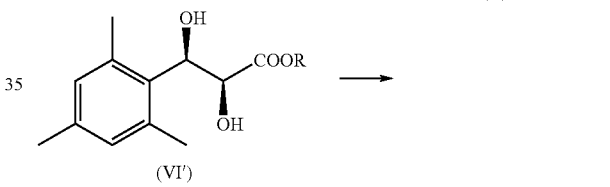

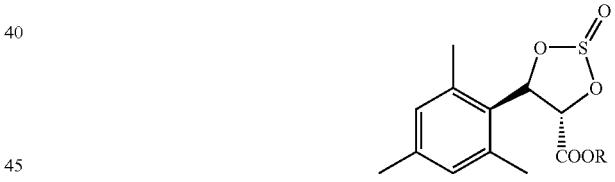

In another preferred embodiment, a compound of formula (VII), wherein R is $(C_1$-$C_8)$-alkyl, is previously subjected to a Sharpless asymmetric dihydroxylation reaction to obtain the compound of formula (VI), alternatively its enantiomer (VI').

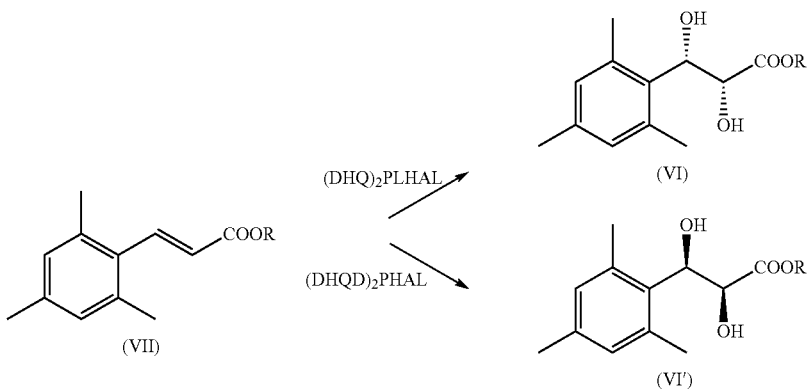

The Sharpless asymmetric dihydroxylation (AD) takes place with an almost quantitative yield and the dihydroxyester (VI), alternatively its enantiomer (VI'), is obtained in optically pure form (generally >99% ee by chiral HPLC). Sharpless dihydroxylation is generally carried out in the presence of osmium tetroxide or potassium osmate, a chiral quinine ligand and an oxidizing agent such as $K_3Fe(CN)_6$ or N-methylmorpholine N-oxide. The obtained compound can be used in the following steps without prior purification. Suitable chiral ligands include but are not limited to hydroquinine 1,4-phthalazinediyl diether ((DHQ)$_2$PHAL) or hydroquinidine 1,4-phthalazinediyl diether ((DHQD)$_2$PHAL) as chiral ligands. Therefore, in the event of using (DHQ)$_2$PHAL, compound (VI) is obtained, and in the event of using (DHQD)$_2$PHAL, compound (VI') is obtained.

Scheme 1 shows a particular embodiment of the invention from the starting product (VIIa).

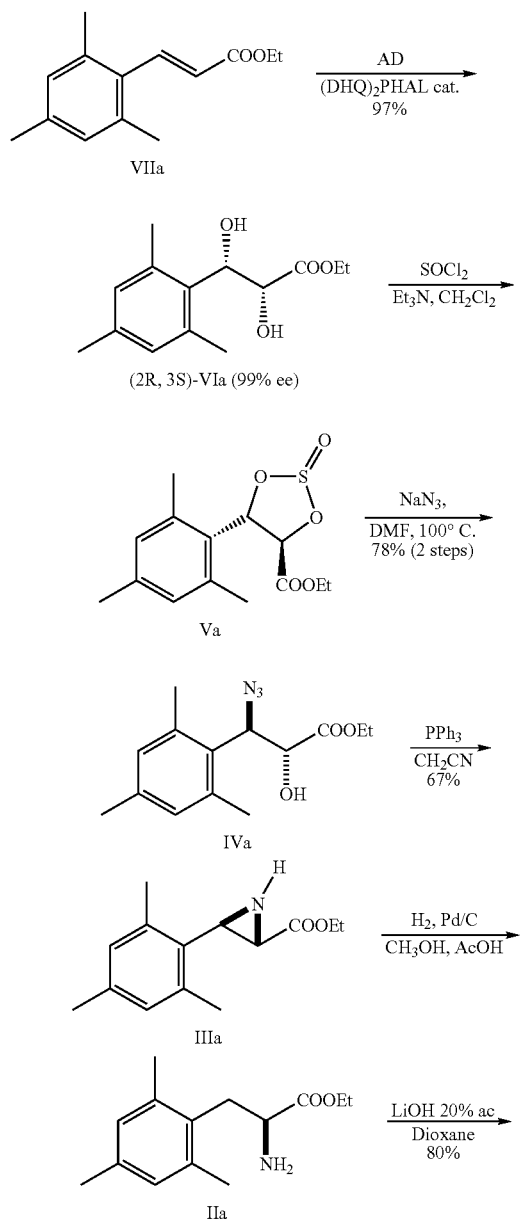

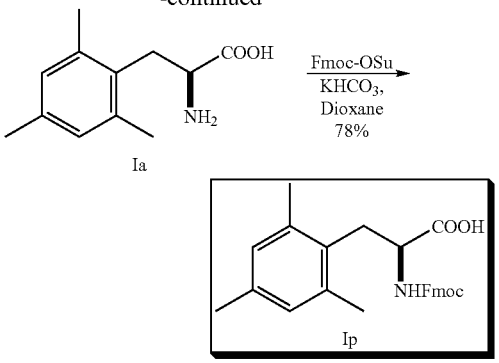

If the opposite configuration of the compound (Ia) or (Ip) is required, the process is carried out similarly starting from the suitably configured compounds.

The starting compound (VII) can be easily obtained from mesityl aldehyde by means of a Horner-Wadsworth-Emmons reaction.

A second aspect of the present invention is to provide the compounds Fmoc-(L)-mesityl alanine and Fmoc-(D)-mesityl alanine, intermediates useful for preparing peptides and peptide analogs with biological activity.

Another aspect of the present invention is to provide a process for preparing peptides in solid phase with one or more mesityl alanine residues, comprising the use of an N-protected amino acid selected from Fmoc-(L)-mesityl alanine, Fmoc-(D)-mesityl alanine, Cbz-(L)-mesityl alanine, Cbz-(D)-mesityl alanine, allyl-(L)-mesityl alanine, allyl-(D)-mesityl alanine, 4-methoxybenzyl-(L)-mesityl alanine, 4-methoxybenzyl-(D)-mesityl alanine 2,4-dimethoxybenzyl-(L)-mesityl alanine, 2,4-dimethoxybenzyl-(D)-mesityl alanine, benzyl-(L)-mesityl alanine, benzyl-(D)-mesityl alanine.

A part of the invention is also the process for preparing peptides in solid phase with one or more mesityl alanine residues, comprising carrying out the process for the stereoselective preparation of a substantially pure enantiomer of a compound of formula (I), alternatively its enantiomer (I'), as defined above in the present description.

The process of the present invention is especially advantageous due to the fact that it makes possible to obtain enantiomerically pure L- and D-mesityl alanine derivatives, which are intermediates useful for preparing peptides and peptide analogs with great biological activity that furthermore have greater stability due to the fact that they incorporate non-natural amino acids. Examples 9 to 11 illustrate by way of example the use of these compounds in the synthesis of peptides in solid phase.

For persons skilled in the art, other objects, advantages and features of the invention will be partly understood partly from the description and partly from the practice of the invention. Throughout the description and claims the word "comprises" and its variants do not intend to exclude other technical features, additives, components or steps.

The following examples are provided by way of illustration and do not intend to limit the present invention.

EXAMPLES

The following non-limiting examples illustrate the invention for a stereoisomeric configuration. When the opposite configuration is required, the invention can be carried out in a similar manner, starting from compounds having a suitable configuration, as would be obvious for a person skilled in the art.

Optical rotations were measured at room temperature (23° C.). The $^1$H NMR spectrum was obtained at 400 MHz with tetramethylsilane as the internal standard. The $^{13}$C NMR was obtained at 100.6 MHz and was referenced to the solvent signal. Signals marked with an asterisk correspond to the rotamers.

Example 1

Preparing ethyl
(2R,3S)-dihydroxy-3-mesitylpropanoate (VIa)

790 mg (1.0 mmol) of (DHQ)$_2$PHAL, 100 g (302 mmol) of K$_3$Fe(CN)$_6$, 41.7 g (302 mmol) of K$_2$CO$_3$, and 149 mg (0.403 mmol) of K$_2$OsO$_4$(OH)$_4$ were introduced in a 2 L reactor and dissolved in 1 L of a H$_2$O:$^t$BuOH (1:1) mixture. Then 9.5 g (100 mmol) of methanesulfonamide were added. It was maintained under stirring for 15 minutes and 22.0 g (100 mmol) of ethyl 3-mesityl-2-propenoate were added next. The reaction mixture was maintained under stirring for 48 hours at room temperature. After this time lapsed, the reaction was stopped by adding Na$_2$SO$_3$ (180 g). Stirring was maintained for 2 hours and the aqueous phase was finally extracted with CH$_2$Cl$_2$ (3×150 mL). All the organic phases were washed with a 2N KOH aqueous solution, dried on MgSO$_4$ and the solvent was evaporated under reduced pressure. 24.3 g (97% of yield) of the product (2R,3S)-VIa were obtained in the form of yellow oil. $[\alpha]_D$=−24.7 (c 0.98, CHCl$_3$). IR (film): ν max 3441 (b), 2978, 1733, 1611, 1190 cm$^{-1}$. $^1$H NMR (400 MHz, CDCl$_3$) δ: 6.80 (s, 2H), 5.18 (d, 1H, J=6.4 Hz), 4.51 (d, 1H, J=6.4 Hz), 4.04 (q, 2H, J=7 Hz), 3.18 (b, 1H), 2.86 (b, 1H), 2.40 (s, 6H), 2.24 (s, 3H), 1.00 (t, 3H, J=7 Hz) ppm. $^{13}$C NMR (100 MHz, CDCl$_3$) δ 173.0 (CO), 137.4 (C), 136.8 (C), 131.8 (C), 130.3 (CH), 73.8 (CH), 73.7 (CH), 61.9 (CH$_2$), 21.0 (CH$_3$), 20.9 (CH$_3$), 13.7 (CH$_3$) ppm. EM (Cl—NH$_3$) m/z: 270.1 [(M+18)$^+$, 100%], 252.1 [(M)$^+$, 60%]. HRMS (Cl+): Calculated for C$_{14}$H$_{20}$O$_4$: 252.1361, 252.1357 found. HPLC: Chiralpack-AD. Hexane/i-PrOH 98:2, 1 mL/min, λ=254 nm, t$_R$ (S,R)=44 min and t$_R$ (R,S)=41 min.

Example 2

Preparing ethyl
(2S,3R)-dihydroxy-3-mesitylpropanoate (VI'a)

The same process was used with ligand (DHQD)$_2$PHAL to obtain ethyl (2S,3R)-dihydroxy-3-mesitylpropanoate with a 95% yield.

The enantiomeric purity of ethyl (2R,3S)-dihydroxy-3-mesitylpropanoate of Example 1 and of ethyl (2S,3R)-dihydroxy-3-mesitylpropanoate of Example 2 was in both cases >99% ee.

Example 3

Preparing (4R,5S)-4-ethoxycarbonyl-5-mesityl-1,3,2-dioxathiolane-2-oxide (Va)

23.5 g (93 mmol) of the diol ethyl (2R,3S)-dihydroxy-3-mesitylpropanoate were dissolved in a reactor in 1.4 L of CH$_2$Cl$_2$. Then 38.9 mL (279 mmol) of NEt$_3$ were added. The reaction mixture was cooled at 0° C. and was maintained under stirring for 5 minutes. Finally 9.5 mL (130.4 mmol) of SOCl$_2$ were added drop-wise and stirring was maintained for 15 minutes at 0° C. After this time, 370 mL of Et$_2$O and 370 mL of water were added. The aqueous phase was extracted with Et$_2$O (3×150 mL) and all the organic phases were washed with a NaCl saturated solution, dried on MgSO$_4$ and the solvent was evaporated under reduced pressure. The sulfite was obtained quantitatively (4R,5S)-Va as an oil. $[\alpha]_D$=−18.8 (c 1.00, CHCl$_3$). IR (film): ν max 2979, 1742, 1216, 1030 cm$^{-1}$. $^1$H NMR (400 MHz, CDCl$_3$) δ: 6.90 (s, 2H), 6.89* (s, 2H), 6.61 (d, 1H, J=8 Hz), 5.95* (d, 1H, J=10 Hz), 5.35* (d, 1H, J=10 Hz), 4.96 (d, 1H, J=8 Hz), 4.30 (dq, 2H, J=20 and 7 Hz), 4.22* (m, 2H), 2.45* (s, 6H), 2.37* (s, 6H), 2.28 (s, 6H), 1.31 (t, 3H, J=7 Hz), 1.22* (t, 3H, J=7 Hz) ppm. $^{13}$C NMR (100 MHz, CDCl$_3$) δ 168.0 (CO), 166.2 (CO), 139.9 (C), 139.8 (C), 138.4 (C), 138.2 (C), 131.0 (CH), 130.9 (CH), 125.6 (C), 122.6 (C), 84.9 (CH), 80.6 (CH), 80.3 (CH), 76.0 (CH), 62.8 (CH$_2$), 21.07 (CH$_3$), 21.06 (CH$_3$), 20.5 (CH$_3$), 20.2 (CH$_3$), 14.2 (CH$_3$), 14.0 (CH$_3$) ppm. EM (Cl—NH$_3$) m/z: 315.6 [(M+17)$^+$, 100%]. HRMS (Cl+): Calculated for C$_{14}$H$_{18}$O$_5$S: 298.0875, 298.0876 found.

Example 4

Preparing ethyl
(2S,3S)-3-azido-2-hydroxy-3-mesitylpropanoate
(IVa)

18.6 g (62.95 mmol) of (4R,5S)-4-ethoxycarbonyl-5-mesityl-1,3,2-dioxathiolane-2-oxide were dissolved in 386 mL of N,N-dimethylformamide (DMF) in a double mouth flask and provided with a coolant, and 8.2 g (125.9 mmol) of NaN$_3$ were added. The reaction mixture was heated at 100° C. for 18 hours. Once this time lapsed, the solvent was removed under reduced pressure and the resulting crude product was dissolved in 310 mL of Et$_2$O and 310 mL of a 20% H$_2$SO$_4$ solution and was maintained under stirring at room temperature overnight. An excess of NaHCO$_3$ saturated solution was added and the aqueous phase was extracted with Et$_2$O (3×150 mL). All the organic phases were dried on MgSO$_4$ and the solvent was evaporated under reduced pressure. The crude product of the reaction was purified by column chromatography (SiO$_2$/NEt$_3$ 2.5% v/v, hexane/AcOEt) and 13.6 g (78% yield) of azido alcohol (2S,3S)-IVa were obtained in the form of yellow oil. $[\alpha]_D$=−126 (c 0.795, CHCl$_3$). IR (film): νmax 3468 (b), 2924, 2105, 1737, 1610, 1257 cm$^{-1}$. $^1$H NMR (400 MHz, CDCl$_3$) δ: 6.88 (s, 2H), 5.19 (d, 1H, J=8.8 Hz), 4.45 (dd, 1H, J=7 and 9 Hz), 4.33 (m, 2H), 2.52 (d, 1H, J=7 Hz), 2.43 (s, 6H), 2.26 (s, 3H), 1.36 (t, 3H, J=7 Hz) ppm. $^{13}$C NMR (100 MHz, CDCl$_3$) δ173.0 (CO), 138.4 (C), 137.6 (C), 130.66 (CH), 130.56 (CH), 128.6 (C), 72.1 (CH), 64.1 (CH), 62.4 (CH$_2$), 21.0 (CH$_3$), 20.9 (CH$_3$), 14.2 (CH$_3$) ppm. EM (Cl—NH$_3$) m/z: 295.3 [(M+18)$^+$, 90%]. HRMS (ESI): Calculated for C$_{14}$H$_{19}$N$_3$O$_3$Na: 300.1315, 300.1318 found.

Example 5

Preparing ethyl
(2R,3S)-3-mesityl-aziridin-2-carboxylate (IIIa)

13.0 g (46.72 mmol) of the azido alcohol ethyl (2S,3S)-3-azido-2-hydroxy-3-mesitylpropanoate were introduced in a flask and dissolved in 282 mL of acetonitrile, next 12.2 g (46.72 mmol) of PPh$_3$ were added. The reaction mixture was stirred for 1 hour at room temperature and 6 hours at reflux temperature. Once this time lapsed, the solvent was removed under reduced pressure and the crude product was purified by column chromatography (SiO$_2$/NEt$_3$ 2.5% v/v, hexane/AcOEt). 7.32 g (67% of yield) of the aziridine (2R,3S)-IIIa were obtained as a yellow oil. $[\alpha]_D$=−131 (c 0.79, CHCl$_3$). IR (film): ν max 3281, 2978, 2922, 1726, 1218, 1201 cm$^{-1}$. $^1$H NMR (400 MHz, CDCl$_3$) δ: 6.82 (s, 2H), 4.31 (m, 2H), 3.16 (d, 1H, J=2 Hz), 2.57 (d, 1H, J=2 Hz), 2.39 (s, 6H), 2.26 (s, 3H), 1.78 (b, 1H), 1.36 (t, 3H, J=7 Hz) ppm. $^{13}$C NMR (100 MHz, CDCl$_3$) δ 172.8 (CO), 137.8 (C), 137.3 (C), 129.0 (CH), 61.8 (CH$_2$), 38.9 (CH), 37.8 (CH), 20.9 (CH$_3$), 20.0 (CH$_3$), 14.4 (CH$_3$) ppm. EM (Cl—NH$_3$) m/z: 233.0 [(M)$^+$, 25%], 146.0 [(M-87)$^+$, 100%]. HRMS (Cl+): Calculated for C$_{14}$H$_{19}$NO$_2$: 233.1416, 233.1418 found. HPLC: Chiralpack-IA. Heptane/i-PrOH 95:5, 1 mL/min, λ=254 nm, t$_R$ (S,R)=19 min and t$_R$ (R,S)=14 min. The enantiomeric purity of ethyl (2R,3S)-3-mesityl-aziridin-2-carboxylate was >99% ee.

Example 6

Preparing (2S)-Mesityl alanine ethyl ester (IIa)

9.9 g (42.42 mmol) of the aziridine ethyl (2R,3S)-3-mesityl-aziridine-2-carboxylate were dissolved in a high pressure reactor in 300 mL of methanol, and 990 mg of Pd/C and 10 mL of acetic acid (84.84 mmol) were added next. The system was purged with vacuum/nitrogen cycles and then the reactor was pressurized with 40 bar of hydrogen. The reaction mixture was maintained under stirring at room temperature for 48 hours. After this time, the catalyst was removed by means of celite filtration and the resulting solution was concentrated under reduced pressure. Compound (IIa) was obtained quantitatively in the form of a yellow solid. Mp 81-83° C. $[\alpha]_D$= −26.7 (c 1.00, CHCl$_3$). IR (film): ν max 2918, 1742, 1612, 1483, 1225. $^1$H NMR (400 MHz, CDCl$_3$) δ: 6.84 (s, 2H), 5.61 (b, 1H), 4.14 (m, 2H), 3.77 (dd, 1H, J=6.4 and 7.6 Hz), 3.08 (m, 2H), 2.94 (m, 2H), 2.31 (s, 6H), 2.25 (s, 3H), 1.18 (t, 3H, J=7 Hz) ppm. $^{13}$C NMR (100 MHz, CDCl$_3$) δ178.9 (CO), 137.1 (C), 136.3 (C), 131.1 (C), 129.5 (CH), 129.5 (CH), 129.2 (C), 61.4 (CH$_2$), 54.1 (CH), 34.6 (CH$_2$), 24.9 (CH$_3$), 21.0 (CH$_3$), 19.8 (CH$_3$), 14.2 (CH$_3$) ppm. EM (ESI+) m/z: 236.2 [(M+H)$^+$, 100%]. HRMS (ESI+): Calculated for C$_{14}$H$_{22}$NO$_2$: 236.1645, 236.1637 found.

Example 7

Preparing (2S)-Mesityl alanine (Ia)

2.0 g (8.50 mmol) of the amino ester (2S)-mesityl alanine ethyl ester were dissolved in a flask in 57 mL of dioxane, and 70 mL of a 20% LiOH aqueous solution are added next. The reaction mixture was stirred at room temperature for 24 hours. Finally the solvent was removed under reduced pressure and the resulting aqueous phase was cooled and acidified with 1M HCl up to pH 7. The precipitation of crystals, which were isolated by means of filtration and subsequent vacuum drying, was observed. 1.3 g (80% of yield) of the amino acid Ia were obtained in the form of a white solid. Mp: 318-320° C. $[\alpha]_D$=−80 (c 1.00, CH$_3$OH). IR (film): vmax 3300, 2973, 1730, 1608, 1409 cm$^{-1}$. $^1$H NMR (400 MHz, CDCl$_3$) δ: 6.75 (s, 2H), 3.27 (t, 1H, J=7.2 Hz), 2.88 (m, 1H), 2.65 (m, 1H), 2.12 (s, 6H), 2.05 (s, 3H) ppm. $^{13}$C NMR (100 MHz, CDCl$_3$) δ181.8 (CO), 137.8 (C), 136.4 (C), 132.2 (C), 128.9 (CH), 56.2 (CH), 34.3 (CH$_2$), 19.9 (CH$_3$), 19.4 (CH$_3$) ppm. EM (Cl+) m/z: 208.3 [(M+H)$^+$, 100%]. HRMS (Cl+): Calculated for C$_{12}$H$_{18}$NO$_2$: 208.1337, 208.1330 found. Anal. Calculated for C$_{27}$H$_{27}$NO$_4$:C, 71.46, H, 8.99, N, 5.95; C, 71.36; H, 8.69; N, 6.39 found.

Example 8

Preparing Fmoc-(L)-mesityl alanine (Ip)

1.08 g (5.22 mmol) of the amino acid L-mesityl alanine were suspended in a flask in 16 mL of a 10% Na$_2$CO$_3$ aqueous solution and it was cooled at 0° C. Then a solution of Fmoc-OSu (2.64 g, 7.83 mmol) in 24 mL of dioxane was added drop-wise. The reaction mixture was stirred 20 hours at room temperature. After this time lapsed, was added was added water (20 mL) and extractions were made with hexane (3×20 mL). The resulting aqueous phase was cooled at 0° C., acidified at pH 2 with 1M HCl and extractions were made with ethyl acetate. The group of resulting organic phases was dried on MgSO$_4$ and the solvent was removed under reduced pressure. The crude product was purified by column chromatography (SiO$_2$/NEt$_3$ 2.5% v/v, hexane/AcOEt) and 1.5 g (68% yield) of Ip were obtained as a white solid. Mp: 187-188° C. $[\alpha]_D$=−26.04 (c 1.00, CHCl$_3$). IR (film): vmax 3321, 2962, 1713, 1450, 1265 cm$^{-1}$. $^1$H NMR (400 MHz, CDCl$_3$) δ: 7.74 (d, 2H, J=7.6 Hz), 7.51 (t, 2H, J=7.6 Hz), 7.40 (t, 2H, J=7.6 Hz), 7.30 (t, 2H, J=7.6 Hz), 6.83 (s, 2H), 5.25 (d, 1H, J=8 Hz), 4.60 (dd, 1H, J=8.0 and 8.4 Hz), 4.30 (m, 1H), 4.14 (m, 1H), 3.18 (m, 2H), 2.32 (s, 6H), 2.21 (s, 6H) ppm. $^{13}$C NMR (100 MHz, CDCl$_3$) δ176.7 (CO), 156.08 (CO), 144.0 (C), 141.5 (C), 137.2 (C), 136.6 (C), 130.0 (C), 129.6 (C), 129.5 (CH), 127.9 (CH), 127.3 (CH), 125.3 (CH), 120.2 (CH), 67.4 (CH$_2$), 53.7 (CH$_2$), 47.3 (CH), 32.5 (CH$_2$), 21.3 (CH$_3$), 20.4 (CH$_3$) ppm. EM (Cl—NH$_3$) m/z: 206.09 [(M−233)$^+$, 82%], 430.2 [(M+H)$^+$, 5%]. HRMS (Cl+): Calculated for C$_{27}$H$_{28}$NO$_4$: 430.2029; 430.2018 found. Anal. calculated for C$_{27}$H$_{27}$NO$_4$: C, 75.50; H, 6.34; N, 3.26; C, 74.94; H, 6.21; N, 3.41 found. HPLC: Chiralcel-AD. Heptane/EtOH/TFA 95:5: 0.2, 1 mL/min, λ=254 nm, t$_R$ (D)=20 min yt$_R$ (L)=26 min. The enantiomeric purity of L-Ip was >99% ee.

Similarly preparing the compound of D-Ip from the compound with a suitable configuration gave rise to the product with an enantiomeric purity of >99% ee.

Example 9

Preparing the Tripeptide Ac-(D-Msa)-Val-Nal-NH$_2$

A syringe was provided with 100 mg (0.06 mmol) of Rink amide resin; it was conditioned with CH$_2$CL$_2$ (5×1 min) and DMF (5×1 min). The synthesis was carried out by means of a standard Fmoc/tBu strategy, using diisopropylcarbodiimide (DIPCDI) as a coupling agent and hydroxybenzotriazole (HOBt) as an additive. Fmoc-3-(1-naphthyl)-L-Ala-OH (Fmoc-Nal) (78.75 mg, 0.18 mmol, 3 eq), Fmoc-L-Val-OH (61.2 mg, 0.18 mmol, 3 eq) and Fmoc-D-Mesityl alanine-OH (Fmoc-D-Msa) (77.4 mg, 0.18 mmol, 3 eq) were used, and the successive incorporation of amino acids was corroborated with ninhydrin tests. After incorporating the third amino acid, the Fmoc group was removed with a mixture of piperidine in DMF and the free amino end was acetylated with Ac$_2$O-diisopropyldiethylamine (DIEA). The resin was finally filtered and thoroughly washed with DMF (5×1 min), CH$_2$CL$_2$ (5×1 min) and methanol (5×1 min). To cleave the tripeptide, it was treated with a trifluoroacetic-water-triisopropylsilane (TFA-H$_2$O-TIS) (95:2.5:2.5) solution for 1 hour and the resulting filtrate was evaporated. It was characterized by reverse-phase chromatography (HPLC) and by EM. After 9 synthesis steps and with no intermediate purification; the obtained crude product had a 39% purity. It was purified with a semi-preparative HPLC (gradient 20-50 in 10 min and 50-100 in 15 min) obtaining 3.4 mg of the tripeptide with an 86% purity (λ=220 nm). HPLC-MS: tr (H$_2$O 0.1% HCOOH; ACN 0.07% HCOOH)=4.830 min. ES+:545.65 (calc. C$_{32}$H$_{40}$N$_4$O$_4$, 544.30).

Example 10

Preparing the tripeptide Ac-(D-Msa)-Val-Lys-NH$_2$

A syringe was provided with 100 mg (0.06 mmol) of Rink amide resin; it was conditioned with CH$_2$CL$_2$ (5×1 min) and DMF (5×1 min). The synthesis was carried out by means of a standard Fmoc/tBu strategy, using DIPCDI as a coupling agent and HOBt as an additive. Fmoc-L-Lys(Boc)-OH (84.33 mg, 0.18 mmol, 3 eq), Fmoc-L-Val-OH (61.2 mg, 0.18 mmol, 3 eq) and Fmoc-D-Msa-OH (77.4 mg, 0.18 mmol, 3 eq) were used, and the successive incorporation of amino acids was corroborated with ninhydrin tests. After incorporating the third amino acid, the Fmoc group was removed with a mixture of piperidine in DMF and the free amino end was acetylated with Ac$_2$O-DIEA. The resin was finally filtered and thoroughly washed with DMF (5×1 min), CH2CL2 (5×1 min) and MeOH (5×1 min). To cleave the tripeptide and remove the Boc protecting group from the side chain of the lys amino acid it was treated with a TFA-H$_2$O-TIS (95:2.5:2.5) solution for 1 hour and the resulting filtrate was evaporated. It was characterized by reverse-phase chromatography (HPLC) and by EM. After 9 synthesis steps and with no intermediate purification; the obtained crude product had 52% purity. It was purified by means of an ion exchange column, obtaining 7.3 mg of the tripeptide with a 96% purity ($\lambda$=220 nm). HPLC-MS: tr (H$_2$O 0.1% HCOOH; ACN 0.07% HCOOH)=3.856 min. ES+:476.57 (calc. C$_{25}$H$_{41}$N$_5$O$_4$, 475.32)

Example 11

Preparing the Tripeptide Ac-(D-Msa)-Asp-Lys-NH$_2$

A syringe was provided with 100 mg (0.06 mmol) of Rink amide resin; it was conditioned with CH$_2$CL$_2$ (5×1 min) and DMF (5×1 min). The synthesis was carried out by means of a standard Fmoc/tBu strategy, using DIPCDI as a coupling agent and HOBt as an additive. Fmoc-L-Lys(Boc)-OH (84.33 mg, 0.18 mmol, 3 eq), Fmoc-L-Asp-OtBu-OH (74.07 mg, 0.18 mmol, 3 eq) and Fmoc-D-Msa-OH (77.4 mg, 0.18 mmol, 3 eq) were used, and the successive incorporation of amino acids was corroborated with ninhydrin tests. After incorporating the third amino acid, the Fmoc group was removed with a mixture of piperidine in DMF and the free amino end was acetylated with Ac$_2$O-DIEA. The resin was finally filtered and thoroughly washed with DMF (5×1 min), CH$_2$CL$_2$ (5×1 min) and MeOH (5×1 min). To cleave the tripeptide and remove the Boc and tBu protecting groups from the side chains of the amino acids it was treated with a TFA-H$_2$O-TIS (95:2.5:2.5) solution for 1 hour and the resulting filtrate was evaporated. It was characterized by reverse-phase chromatography (HPLC) and by EM. After 9 synthesis steps and with no intermediate purification; the obtained crude product had 71% purity. It was purified by means of an ion exchange column, obtaining 17.0 mg of the tripeptide with a 94% purity ($\lambda$=220 nm). HPLC-MS: tr (H$_2$O 0.1% HCOOH; ACN 0.07% HCOOH)=2.543 min. ES+: 492.58 (calc. C$_{24}$H$_{37}$N$_5$O$_6$, 491.27).

The invention claimed is:

1. A process for the stereoselective preparation of a substantially pure enantiomer of a compound of formula (I), alternatively its enantiomer (I'),

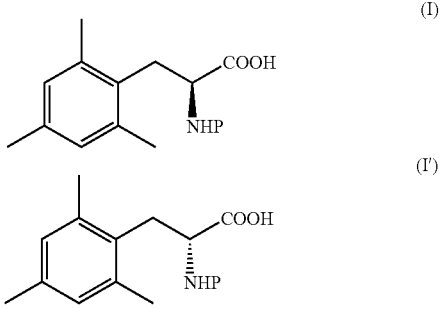

wherein P is hydrogen or an amine protecting group, comprising the following steps:

a) subjecting a compound of formula (III), alternatively its enantiomer (III'), to hydrogen in the presence of palladium/activated carbon to obtain the compound of formula (II), alternatively its enantiomer (II'); wherein R is (C$_1$-C$_8$)-alkyl;

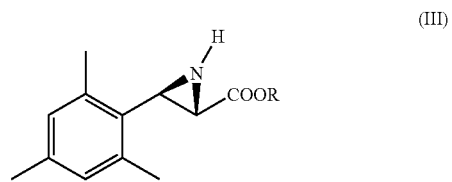

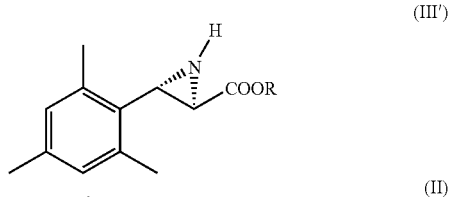

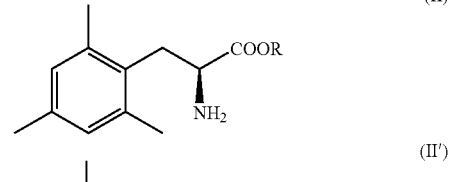

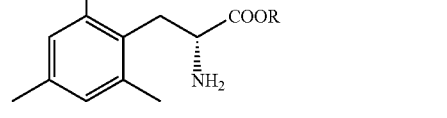

b) subjecting the compound of formula (II), alternatively its enantiomer (II'), to a hydrolysis reaction to obtain a compound of formula (I), alternatively its enantiomer (I'), wherein P is hydrogen and, optionally, subjecting said compound (I), alternatively its enantiomer (I'), to an amino group protection reaction.

2. The process for the stereoselective preparation according to claim 1, wherein P is selected from the group consisting of 9-fluorenylmethyl carbamate (Fmoc), t-butoxycarbonyl (BOC), benzyloxycarbonyl (Cbz), allyl, 4-methoxybenzyl, 2,4-dimethoxybenzyl and benzyl.

3. The process for the stereoselective preparation according to claim 1, wherein the hydrolysis reaction is carried out in basic medium.

4. The process for the stereoselective preparation according to claim 3, wherein the base of the hydrolysis reaction is a hydroxide of an alkali metal.

5. The process for the stereoselective preparation according to claim 1, wherein the compound of formula (IV), alternatively its enantiomer (IV'), wherein R is $(C_1-C_8)$-alkyl, reacts

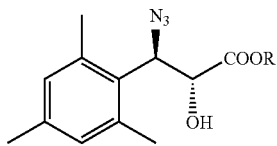
(IV)

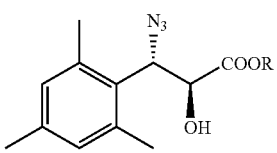
(IV')

with a phosphine of formula $P(R_1)_3$, wherein $R_1$ is independently selected from the group consisting of $(C_1-C_8)$-alkyl, $(C_1-C_8)$-cycloalkyl, optionally substituted phenyl, optionally substituted $(CH_2)_n$-phenyl, wherein n is an integer from 1 to 4, and the substituents of the radicals with benzene rings are independently selected from the group consisting of $(C_1-C_8)$-alkyl, $(C_1-C_8)$-alkoxyl or halogen, to obtain the compound of formula (III), alternatively its enantiomer (III'),

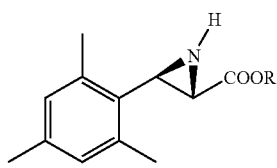
(III)

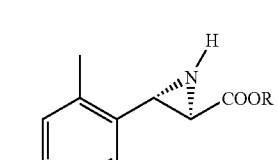
(III')

wherein in formulas (III), (III'), (IV) and (IV') R is $(C_1-C_8)$-alkyl.

6. The process for the stereoselective preparation according to claim 5, wherein the compound of formula (V), alternatively its enantiomer (V'), reacts

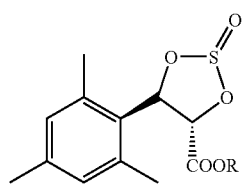
(V)

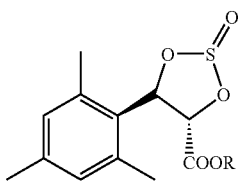
(V')

with an alkali or alkaline-earth metal azide to obtain the compound of formula (IV), alternatively its enantiomer (IV'),

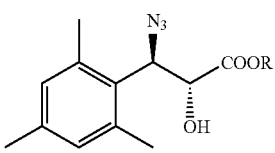
(IV)

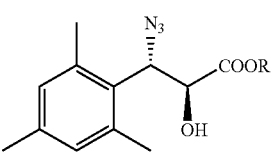
(IV')

wherein in formulas (IV), (IV'), (V) and (V') R is $(C_1-C_8)$-alkyl.

7. The process for the stereoselective preparation according to claim 6, wherein the compound of formula (VI), alternatively its enantiomer of formula (VI'), reacts

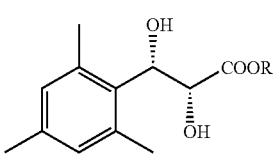
(VI)

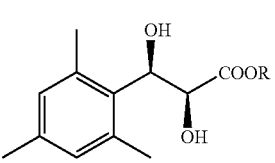
(VI')

with a thionyl halide to obtain the compound of formula (V), alternatively its enantiomer (V'),

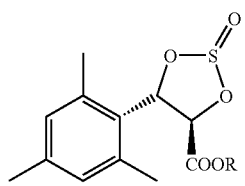
(V)

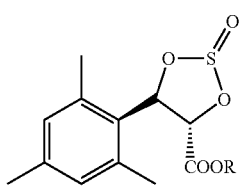 (V')

wherein in formulas (V), (V'), (VI) and (VI') R is (C$_1$-C$_8$)-alkyl.

8. The process for the stereoselective preparation according to claim 7, wherein the compound of formula (VII)

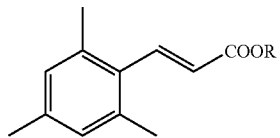 (VII)

is subjected to a Sharpless asymmetric dihydroxylation reaction using a suitable chiral ligand to obtain the compound of formula (VI), or alternatively the compound of formula (VI'),

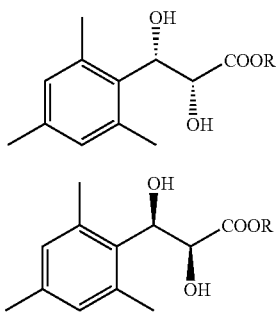

wherein in formulas (VI), (VI') and (VII) R is alkyl.

9. The process for the stereoselective preparation according to claim 8, wherein the suitable chiral ligand is selected from the group consisting of hydroquinine 1,4-phthalazinediyl diether ((DHQ)$_2$PHAL) to obtain the compound of formula (VI) or hydroquinidine 1,4-phthalazinediyl diether ((DHQD)$_2$PHAL) to obtain the compound of formula (VI').

* * * * *